United States Patent [19]
Wolf

[11] Patent Number: 5,278,144
[45] Date of Patent: Jan. 11, 1994

[54] ANTITHROMBOSIS AGENTS

[75] Inventor: David Wolf, Palo Alto, Calif.

[73] Assignee: Cor Therapeutics, Inc., South San Francisco, Calif.

[21] Appl. No.: 578,646

[22] Filed: Sep. 4, 1990

[51] Int. Cl.$^5$ .................... C07K 7/10; A61K 37/02
[52] U.S. Cl. .................... 514/12; 424/94.64; 435/69.1; 435/69.2; 435/69.6; 514/2; 514/8; 530/384; 530/395
[58] Field of Search ............... 514/12, 8, 2; 530/395, 530/384; 435/69.1, 69.2, 69.6, 212; 424/94.64

[56] References Cited

U.S. PATENT DOCUMENTS 5,120,537 6/1992 Esmon et al. .................... 424/94.64

FOREIGN PATENT DOCUMENTS 0255206 2/1988 European Pat. Off.

OTHER PUBLICATIONS

Hoover et al., *Cell* (1978) 14:423–428.
Etingin et al., *Cell* (1990) 61:657–662.
Davie, E. W., *Haemostasis and Thrombosis*, Second Edition, R. W. Colman et al., eds., (1987) J. B. Lippencott, Philadelphia, Pa., Chapter 16, pp. 242–267.
Furie et al., *Cell* (1988) 53:505–518.
Steinberg et al., *Haemostasis and Thrombosis*, Second Edition, R. W. Colman et al., eds., (1987) J. B. Lippencott, Philadelphia, Pa., Chapter 7, pp. 112–119.
Di Scipio et al., *Biochemistry* (1977) 16:5253–5260.
Nesheim et al., *J. Biol. Chem.* (1979) 254:10952–10962.
Nesheim et al., *J. Biol. Chem.* (1981) 256(13):6537–6540
Skogen et al., *J. Biol. Chem.* (1984) 259(4):2306–2310.
Krishnaswamy et al., *J. Biol. Chem.* (1988) 263(8):3823–3824.
Husten et al., *J. Biol. Chem.* (1987) 262(27):12953–12961.
Girard et al., *Nature* (1989) 338:518–520.
Girard et al., *Science* (1990) 248:1421–1424.
Donwiddie et al., *J. Biol. Chem.* (1989) 264:16694–16699.
Waxman et al., *Science* (1990) 248:593–596.
Bajaj et al., *J. Biol. Chem.* (1973) 248(22):7729–7741.
Colman et al., *Haemostasis and Thrombosis*, Second Edition, R. W. Colman et al., eds., (1987) J. B. Lippencott, Philadelphia, Pa., Section 1, Chapter 1, pp. 3–17.
Kaul et al., *Gene* (1986) 41:311–314.

*Primary Examiner*—Lester L. Lee
*Attorney, Agent, or Firm*—Morrison & Foerster

[57] ABSTRACT

Analogs of Factor Xa (Factor Xai) which are inactive as proteases in the prothrombinase reaction are useful in treatment of diseases characterized by thrombosis. These antithrombotic agents can be conveniently prepared using recombinant techniques.

10 Claims, 17 Drawing Sheets

```
   1  GTCGACTCTA  GAGGGGCTGG  CAGGAATTCC  GCATGGGGCG  CCCACTGCAC
  51  CTCGTCCTGC  TGAGTGCCTG  CCTGGCTGGC  CTCCTGCTGC  TCGGGGAAAG
 101  TCTGTTCATC  CGCAGGGAGC  AGGCCAACAA  CATCCTGGCG  AGGGTCACGA
 151  GGGCCAATTC  CTTTCTTGAA  GAGATGAAGA  AAGGACACCT  CGAAAGAGAG
 201  TGCATGGAAG  AGACCTGCTC  ATACGAAGAG  GCCCGCGAGG  TCTTTGAGGA
 251  CAGCGACAAG  ACGAATGAAT  TCTGGAATAA  ATACAAAGAT  GGCGACCAGT
 301  GTGAGACCAG  TCCTTGCCAG  AACCAGGGCA  AATGTAAAGA  CGGCCTCGGG
 351  GAATACACCT  GCACCTGTTT  AGAAGGATTC  GAAGGCAAAA  ACTGTGAATT
 401  ATTCACACGG  AAGCTCTGCA  GCCTGGACAA  CGGGGACTGT  GACCAGTTCT
 451  GCCACGAGGA  ACAGAACTCT  GTGGTGTGCT  CCTGCGCCCG  CGGGTACACC
 501  CTGGCTGACA  ACGGCAAGGC  CTGCATTCCC  ACAGGGCCCT  ACCCCTGTGG
 551  GAAACAGACC  CTGGAACGCA  GGAAGAGGTC  AGTGGCCCAG  GCCACCAGCA
 601  GCAGCGGGGA  GGCCCCTGAC  AGCATCACAT  GGAAGCCATA  TGATGCAGCC
 651  GACCTGGACC  CCACCGAGAA  CCCCTTCGAC  CTGCTTGACT  TCAACCAGAC
 701  GCAGCCTGAG  AGGGGCGACA  ACAACCTCAC  CAGGATCGIG  GGAGGCCAGG
 751  AATGCAAGGA  CGGGGAGTGT  CCCTGGCAGG  CCCTGCTCAT  CAATGAGGAA
 801  AACGAGGGTT  TCTGTGGTGG  AACTATTCTG  AGCGAGTTCT  ACATCCTAAC
 851  GGCAGCCCAC  TGTCTCTACC  AAGCCAAGAG  ATTCAAGGTG  AGGTAAGGGG
 901  ACCGGAACAC  GGAGCAGGAG  GAGGGCGGTG  AGGCGGTGCA  CGAGGTGGAG
 951  GTGGTCATCA  AGCACAACCG  GTTCACAAAG  GAGACCTATG  ACTTCGAGAT
1001  CGCCGTGCTC  CGGCTCAAGA  CCCCCATCAC  CTTCCGCATG  AACGTGGCGC
1051  CTGCCTGCCT  CCCCGAGCGT  GACTGGGCCG  AGTCCACGCT  GATGACGCAG
1101  AAGACGGGGA  TTGTGAGCGG  CTTCGGGCGC  ACCCACGAGA  AGGGCCGGCA
1151  GTCCACCAGG  CTCAAGATGC  TGGAGGTGCC  CTACGTGGAC  CGCAACAGCT
1201  GCAAGCTGTC  CAGCAGCTTC  ATCATCACCC  AGAACATGTT  CTGTGCCGGC

1301  CGTCACCCGC  TTCAAGGACA  CCTACTTCGT  GACAGGCATC  GTCAGCTGGG
1351  GAGAGGGCTG  TGCCCGTAAG  GGGAAGTACG  GGATCTACAC  CAAGGTCACC
1401  GCCTTCCTCA  AGTGGATCGA  CAGGTCCATG  AAAACCAGGG  GCTTGCCCAA
1451  GGCCAAGAGC  CATGCCCCGG  AGGTCATAAC  GTCCTCTCCA  TTAAAGTGAG
1501  CGTCCTCTCC  ATCCCACTCA  AAAAAAAAAA  AAAAAAAAAA  AAAAAAAAAA
```

Fig. 4

FACTOR X ENZYMATIC ACTIVITIES

| | Kcat($s^{-1}$) | Km (μm) | Specificity Constant<br>Kcat/Km ($s^{-1}$ $M^{-1}$) |
|---|---|---|---|
| Native forms | | | |
| X | 64 | 131 | 489 x $10^3$ |
| Xa | 367 | 184 | 1996 x $10^3$ |
| Precursor construct | | | |
| rX | 22 | 134 | 167 x $10^3$ |
| rX'Δ0 | N.D. | - | - |
| rX'Δ1 | N.D. | - | - |
| rX'Δ2 | 17 | 149 | 115 x $10^3$ |
| rX'Δ3 | N.D. | - | - |
| rXiN$_{88}$A$_{185}$ | N.D. | - | - |
| rXiA$_{185}$ | N.D. | - | - |
| rX'i(Δ2)N$_{88}$A$_{185}$ | N.D. | - | - |
| rX'i(Δ2)N$_{88}$ | N.D. | - | - |
| Control CHO medium | N.D. | - | - |

N.D. = not detected, Kcat ≤ .1 in 14 hrs - 16 hrs assay.

FIG. 8

ANTITHROMBOSIS AGENTS

TECHNICAL FIELD

The invention relates to peptide drugs for prevention or treatment of thrombosis. More specifically, the invention concerns analogs of Factor Xa which lack protease activity and which interfere with the ability of endogenous Factor Xa to effect the conversion of prothrombin to thrombin.

BACKGROUND ART

Thrombin is a multifunctional protease that regulates several key biological processes. For example, thrombin is among the most potent of the known platelet activators. In addition, thrombin is essential for the cleavage of fibrinogen to fibrin to initiate clot formation. These two elements are involved in normal hemostasis but in atherosclerotic arteries can initiate the formation of a thrombus, a major factor in pathogenesis of vasoocclusive conditions such as myocardial infarction, unstable angina, nonhemorrhagic stroke and reocclusion of coronary arteries after angioplasty or thrombolytic therapy. Thrombin is also a potent inducer of smooth cell proliferation and may therefore be involved in a variety of proliferative responses such as restenosis after angioplasty and graft-induced atherosclerosis. In addition, thrombin is chemotactic for leukocytes and may therefore play a role in inflammation (Hoover, R. J., et al. Cell (1978) 14:423; Etingin, O. R., et al., Cell (1990) 61:657.) These observations indicate that inhibition of thrombin formation or inhibition of thrombin itself may be effective in preventing or treating thrombosis, limiting restenosis and controlling inflammation.

The formation of thrombin is the result of the proteolytic cleavage of its precursor prothrombin at the Arg-Thr linkage at positions 271–272 and the Arg-Ile linkage at positions 320–321. This activation is catalyzed by the prothrombinase complex, which is assembled on the membrane surfaces of platelets, monocytes, and endothelial cells. The complex consists of Factor Xa (a serine protease), Factor Va (a cofactor), calcium ions and the acidic phospholipid surface. Factor Xa is the activated form of its precursor, Factor X, which is secreted by the liver as a 58 kd precursor and is converted to the active form, Factor Xa, in both the extrinsic and intrinsic blood coagulation pathways. It is known that the circulating levels of Factor X, and of the precursor of Factor Va, Factor V, are on the order of $10^{-7}$M. There has been no determination of the levels of the corresponding active Factors Va and Xa.

The complete amino acid sequences of human Factor X and Factor Xa are known. FIG. 1 shows the complete sequence of the precursor form of Factor X as described by Davie, E. W., in Hemostasis and Thrombosis, Second Edition, R. W. Coleman et al. eds. (1987) p. 250. Factor X is a member of the calcium ion binding, gamma carboxyglutamyl (Gla)-containing, vitamin K dependent, blood coagulation glycoprotein family, which also includes Factors VII and IX, prothrombin, protein C and protein S (Furie, B., et al., Cell (1988) 53:505).

As shown in FIG. 1, the mature Factor X protein is preceded by a 40-residue pre-pro leader sequence which is removed during intracellular processing and secretion. The mature Factor X precursor of Factor Xa is then cleaved to the two-chain form by deletion of the three amino acids RKR shown between the light chain C-terminus and activation peptide/heavy chain N-terminus. Finally, the two chain Factor X is converted to Factor Xa by deletion of the "activation peptide" sequence shown at the upper right-hand portion of the figure (numbered 1–52), generating a light chain shown as residues 1–139, and a heavy chain shown as residues 1–254. These are linked through a single disulfide bond between position 128 of the light chain and position 108 of the heavy chain. As further indicated in the figure, the light chain contains the Gla domain and a growth factor domain; the protease activity resides in the heavy chain and involves the histidine at position 42, the aspartic acid at position 88, and a serine at position 185, circled in the figure.

There are two known pathways for the activation of the two-chain Factor X in vivo. Activation must occur before the protease is incorporated into the prothrombinase complex (Steinberg, M., et al., in Hemostasis and Thrombosis, Coleman, R. W., et al. eds. (1987) J. B. Lippencott, Philadelphia, Pa., p. 112). In the intrinsic pathway, Factor X is cleaved to release the 52-amino acid activation peptide by the "tenase" complex which consists of Factor IXa, Factor VIII and calcium ions assembled on cell surfaces. In the extrinsic pathway, the cleavage is catalyzed by Factor VIIa which is bound to a tissue factor on membranes. Of interest herein, however, is the ability to convert Factor X to Factor Xa by in vitro cleavage using a protease such as that contained in Russell's viper venom. This protease is described by DiScipio, R. G., et al., Biochemistry (1977) 6:5253.

The formation of the prothrombinase complex (which is 278,000 fold faster in effecting the conversion of prothrombin to thrombin than Factor Xa in soluble form) has been studied (Nesheim, H. E., et al., J Biol Chem (1979) 254:10952). These studies have utilized the active site-specific inhibitor, dansyl glutamyl glycyl arginyl (DEGR) chloromethyl ketone, which covalently attaches a fluorescent reporter group into Factor Xa. Factor Xa treated with this inhibitor lacks protease activity, but is incorporated into the prothrombinase complex with an identical stoichiometry to that of Factor Xa and has a dissociation constant of $2.7 \times 10^{-6}$M (Nesheim, M. E., J Biol Chem (1981) 256:6537–6540; Skogen, W. F., et al., J Biol Chem (1984) 256:2306–2310; Krishnaswamy, S., et al., J Biol Chem (1988) 263:3823–3824; Husten, E. J., et al., J Biol Chem (1987) 262:12953–12961).

Known methods to inhibit the formation of the prothrombinase complex include treatment with heparin and heparinlike compounds. This results in inhibition of the formation of the complex by antithrombin III in association with the heparin. Other novel forms of Factor Xa inhibition include lipoprotein-associated coagulation inhibitor (LACI) (Girard, T. J., et al., Nature (1989) 338:518; Girard, T. J., et al., Science (1990) 248:1421), leech-deriVed antistatin (Donwiddie, C. et al. J Biol Chem (1989) 264:16694), and tick-derived TAP (Waqxman, L., et alt., Science (1990) 248:593). Alternatively, agents which inhibit the vitamin K-dependent Gla conversion enzyme, such as coumarin, have been used. None of these approaches have proved satisfactory due to lack of specificity, the large dosage required, toxic side effects, and the long delay in effectiveness.

Accordingly, the invention offers an alternative approach of enhanced specificity and longer duration of action in inhibiting the formation of an active prothrombinase complex.

DISCLOSURE OF THE INVENTION

The invention provides effective therapeutic agents for the prevention and treatment of thrombus formation and other pathological processes in the vasculature induced by thrombin such as restenosis and inflammation. This is highly significant as thrombus formation is the leading cause of death in Western societies, and restenosis is an expanding problem with increased use of angioplasty and other invasive procedures. The therapeutic materials of the invention are inactive forms of human Factor Xa which are nevertheless capable of incorporation into the prothrombinase complex, thus preventing the formation of active prothrombinase complex from endogenous Factor Xa. These pharmaceuticals are especially useful in acute settings to prevent thrombosis. This includes preventing thrombus formation in the coronary arteries of patients with rest angina, preventing rethrombosis after thrombolysis, and prevention of thrombosis during complicated angioplasties. These pharmaceuticals will also be useful in preventing smooth muscle cell proliferation following angioplasty or other vascular invasive procedures. The inventive therapeutics offer considerable advantage over the now standard treatment which involves heparin (Hanson, R. S., et al., *Proc Natl Acad Sci* (1988) 85:3184). The compounds of the invention are double- or single-chain polypeptides which are capable of participation in the prothrombinase complex, but which result in an inactive complex.

In one aspect, the invention is directed to a two-chain polypeptide, designated Factor Xai, which is capable of forming the prothrombinase complex, but which results in a complex that lacks proteolytic activity. This two-chain polypeptide may be formed from one of two types of novel precursors. One type, designated herein Factor Xi, has substantially the amino acid sequence of Factor X, but is modified as described herein so as to result in an inactive two-chain polypeptide, Factor Xai, when cleaved by normal coagulation processing proteases or by in vitro treatment with Factor X activator from viper venom. The other type, designated herein Factor X'i, is a truncated form of single chain Factor X wherein the proteolytic cleavage site (or portion or extension thereof) at the C-terminus of the light chain, shown as RKR in FIG. 1, is ligated directly (with the optional addition of one or several amino residues) to the N-terminus of the activated form of the heavy chain as shown in one embodiment in FIG. 3. Upon cleavage, Factor X'i also results in the two-chain Factor Xai of the invention which results in a prothrombinase complex lacking proteolytic activity. Of course, the active cofactor, Factor Xa, could also be generated by using the analogous precursors of the Factor X' type illustrated in FIG. 2.

Thus, in other aspects, the invention is directed to the Factor Xai two-chain prothrombinase complex, and to the novel precursors of the Factor Xai therapeutic proteins, to the DNA sequences encoding them, and to recombinant materials and methods generally which permit their production.

Other aspects of the invention include pharmaceutical compositions of the therapeutically useful Factor Xai proteins and to methods to prevent or treat thrombosis or other pathological events initiated by thrombin using these compositions.

BRIEF DESCRIPTION OF THE DRAWINGS

FIG. 4 shows the cDNA sequence encoding Factor X.

FIG. 8 is a table showing enzymatic activities of native and recombinantly produced Factor Xa forms.

MODES OF CARRYING OUT THE INVENTION

Figure 1:
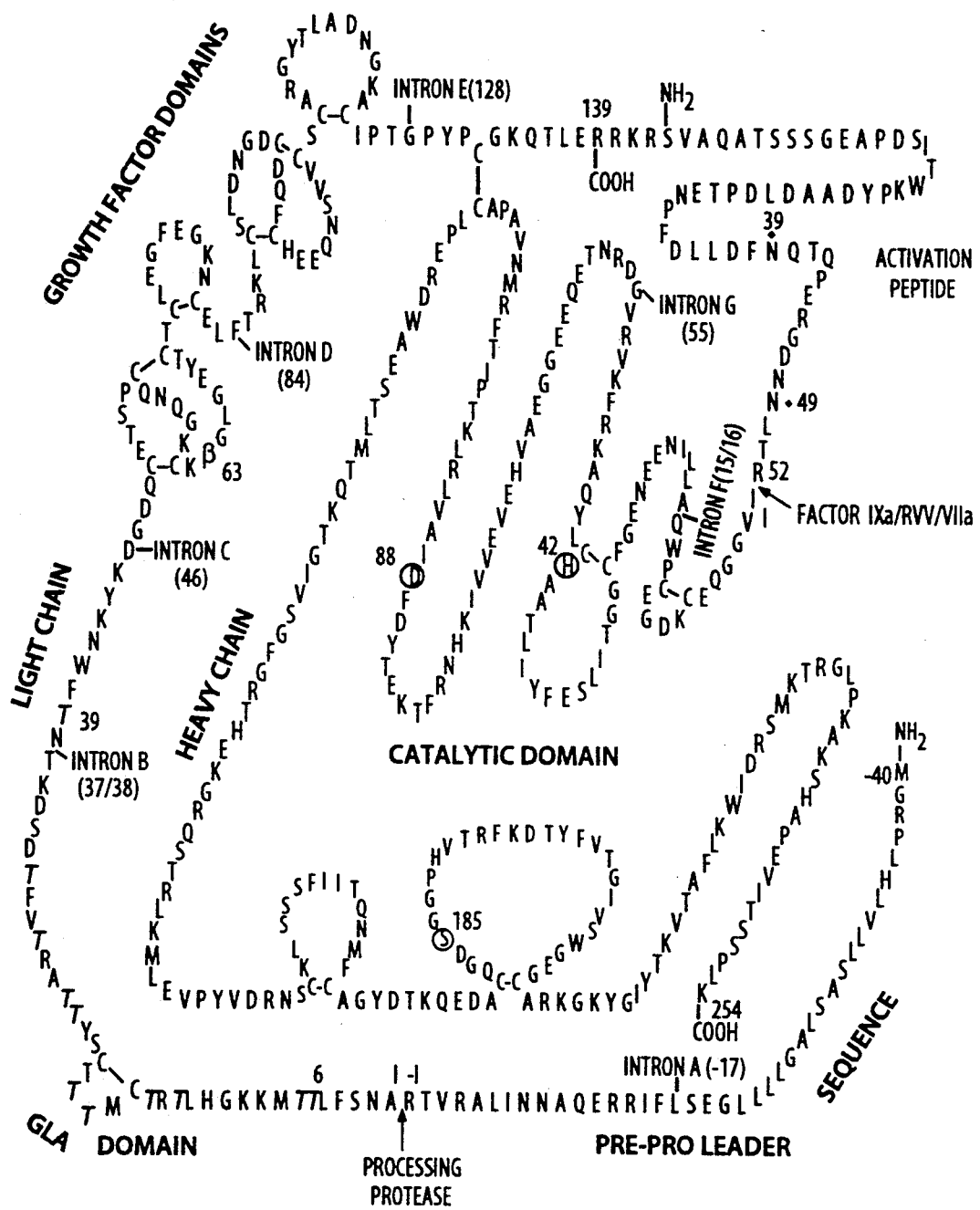
FIG. 1 shows the structure of human Factor X and its relevant cleavage sites as described in the prior art.
Figure 2:
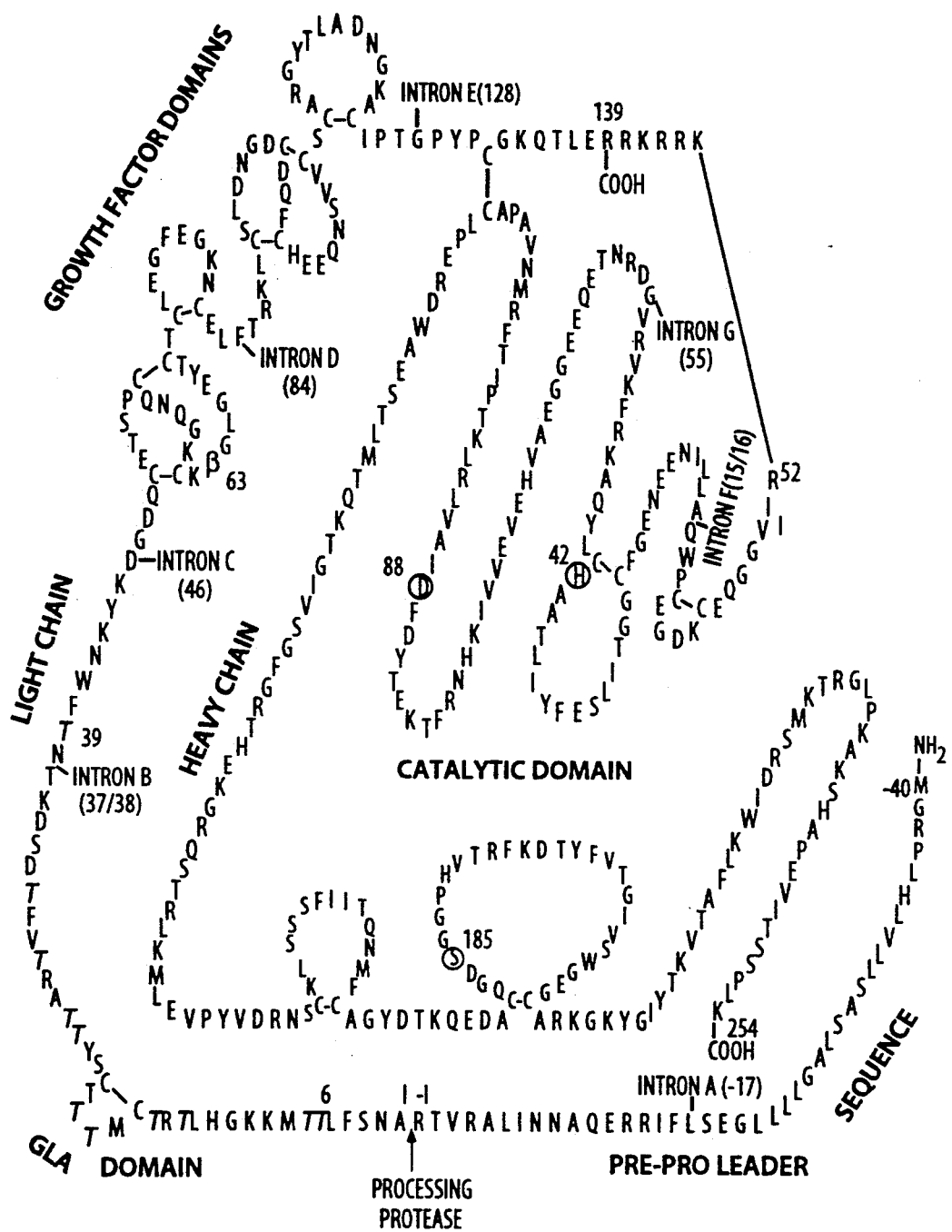
FIG. 2 shows the structure of one embodiment of a single-chain Factor X' which is a precursor to yield a two-chain cleavage product that will participate in prothrombinase complex formation. The form shown in this figure will produce a two-chain peptide which retains proteolytic activity in the complex; a modified form, as described below, is catalytically inactive.
Figure 3:
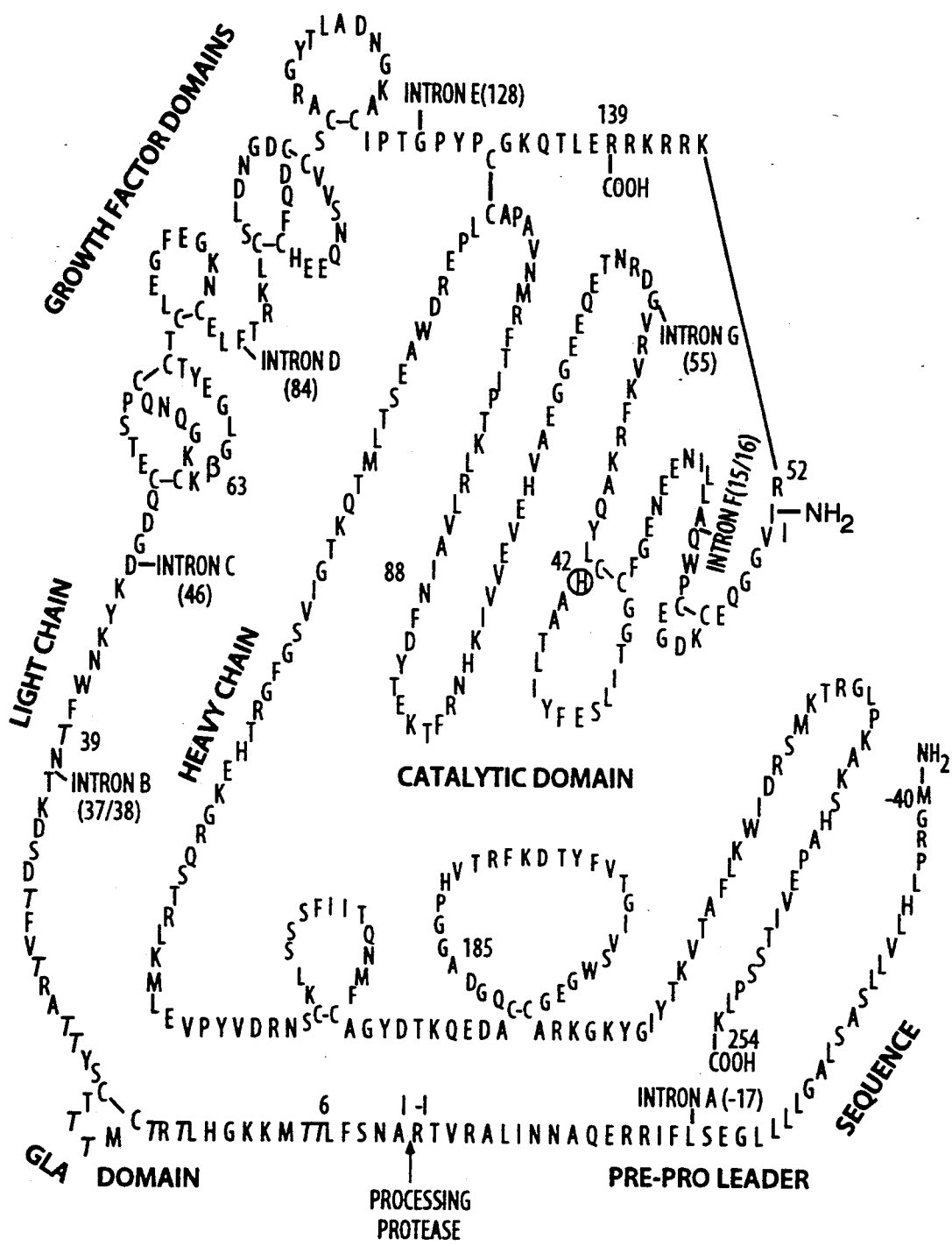
FIG. 3 shows one embodiment of Factor X'i.

In general, the invention encompasses the therapeutically useful two-chain polypeptide, designated Factor Xai herein, and the single-chain precursors of this two-chain protein. These peptides are about 80% homologous, preferably about 90% homologous to the amino acid sequences shown at positions 1–139 (light chain) and 1–254 (heavy chain) in FIG. 1. It should be noted that in FIG. 1, the pre-pro leader sequence is numbered −40 through −1, prior to the numbering beginning at the N-terminus of the light chain. The light chain is numbered 1–139. The intervening tripeptide RKR, which, in mature Factor X, is deleted, is not numbered. The activation peptide beginning subsequent to this intervening tripeptide is numbered 1–52; the isoleucine referred to hereinbelow as "position 53" of the activation peptide is, in fact, the first amino acid of the heavy chain in the activated form. This restarts the numbering shown in the figure, and the heavy chain is numbered 1–254.

The embodiments of the two-chain peptide, Factor Xai, are effective in forming the prothrombinase complex, as determined by their ability to inhibit (or compete with) the formation of the native prothrombinase complex involving Factor Xa. Their ability to inhibit prothrombinase complex formation can be determined conveniently by the method of Krishnaswamy, S., *J Biol Chem* (1988) 263:3823–3834, cited above. However, when incorporated into the prothrombinase complex, the complex fails to show its proteolytic activity, as determined by the method of van Dieijen G., et al. *J Biol Chem* (1981) 256:3433 or of Skogen, W. F., et al., *J Biol Chem* (1984) 256:2306. These Factor Xai proteins may or may not be immunoreactive with antibodies raised against native Factor Xa or against Factor X, including commercially available antibodies specific for human Factor X. The Factor Xai proteins are antithrombotic materials.

The invention is also directed to precursors of the foregoing inactive competitors with Factor Xa. One group of these precursors are novel modified forms of Factor X designated Factor Xi, wherein one or more of the residues at position 42, 88 or 185 of the heavy chain are converted to alternate amino acid residues, thus inactivating the proteolytic properties of the peptide. The modified forms of Factor X contain at a minimum the light chain sequence and the heavy chain sequence to which is attached the activation peptide. The intervening tripeptide (between the C-terminus of the light chain the N-terminus of the activation peptide) and the pre-pro leader sequence may or may not be present. Thus, the Factor X may either be a single-chain protein (when the tripeptide is included) or a two-chain precursor of Factor Xa (when the tripeptide has been deleted).

Preferably, the alteration at the residues of the protease active site is either a deletion, or a conversion to a conservative, substituted amino acid so as to maintain the three-dimensional conformation of the two-chain protein. By "conservative" is meant a substitution which maintains the correct conformation, rather than a substitution which maintains the correct activity. Thus, the histidine residue at position 42 is preferably replaced by phenylalanine; the aspartic acid at position 88 is preferably replaced by asparagine or glutamine, and the serine residue at position 185 is preferably replaced by alanine or glycine.

Another group of precursors to the antithrombotic dimeric peptides of the invention is designated Factor X'i. In Factor X'i precursors, at least a substantial portion of the activation peptide, preferably the entire activation peptide is deleted. The precursors to the two-chain form of Factor X'i, however, must retain a proteolytic cleavage site between the light and heavy chains. Therefore, amino acids subject to endogenous proteolysis are conveniently included in a single-chain precursor form which extends the carboxy terminus of the light chain by virtue of the cleavage site to the N-terminus of the heavy chain. A typical embodiment of the single-chain precursor (including the pre-pro leader) to the two-chain Factor X'i, which will now automatically be activated by virtue of the absence of the activation peptide sequence (thus, becoming a Factor Xai) is shown in FIG. 3. In this embodiment, the hexapeptide sequence RKRRKR connects the C-terminus of the light chain directly to the isoleucine residue at the N-terminus of the heavy chain. Cleavage of this single-chain Factor X'i results in X'ai. In constructing such modified X'i type precursors, a hydrophobic amino acid must be retained at the N-terminus of the heavy chain (natively isoleucine). See, for example, Dayhoff, M. O., "Atlas of Protein Sequence and Structure" (1972) 5: 89-99 (Biomed. Res Foundation, Wash. D.C.) and Greer, J., *J. Molec. Biol.* (1981) 153:1043-1053.

It is evident that the single-chain Factor X' precursors are also novel and, when cleaved by proteolysis, yield Factor Xa, the normal enzymatically-active. form of the dimeric protein. This corresponding construction is shown in FIG. 2.

Thus, when the single-chain precursors of either Factor Xa or Factor Xai are produced recombinantly in suitable host cells, the endogenous enzymes of the host cell may (1) cleave the single-chain precursor Factor X or X' to a two-chain form and, in the case of single-chain Factor X or Xi, further activate the factor by cleavage of the activation peptide in the case of Factor X' single-chain precursors, there is no activation peptide present, so the single-chain precursor will automatically be activated when cleaved into a dimeric peptide. For Factor X precursors, the double-chain form containing the activation peptide may also be cleaved in vitro using a suitable protease, such as the Factor X activator of Russell's viper venom.

To summarize the terminology used in this application, the following glossary may be useful:

"Factor X" refers to the native or recombinantly produced single- or two-chain Factor X sequence, essentially as shown in FIG. 1, containing at a minimum the heavy chain to which is attached the activation peptide, at its N-terminus and the light chain. These may or may not be linked through a cleavage sequence as indicated in the figure. "rX" refers specifically to the recombinantly produced form of this factor.

"Factor Xi" refers to the recombinantly produced form of Factor X which lacks proteolytic activity by virtue of the modification of the active site as described above. The designation "rXi" is also used for this protein.

"Factor Xa" refers to native or recombinantly produced, enzymatically active dimer containing light and heavy chain only. The activation peptide is not present in this complex. "rXa" refers specifically to this complex when produced recombinantly.

"Factor Xai" refers to the modified form of Factor Xa which is activated in the sense that it combines to form the prothrombinase complex, but which has no serine protease activity by virtue of the modification of its active site. As this protein is produced only by recombinant methods, "rXai" is also used to designate this complex.

"Factor X'" refers to a modified, single-chain form of Factor X which includes only the light chain, heavy chain, and an intermediate, specific proteolytic cleavage site, such as that shown in FIG. 2. This single-chain precursor may also contain the pre-pro sequence. As it is a result only of recombinant production, it is also designated "rX'." When cleaved by a protease so as to become activated, the products are indistinguishable from Factor Xa (or rXa) and, accordingly, this terminology is again used.

Similarly, "Factor X'i" refers to a modified form of Factor X' which has been inactivated at its catalytic site as described above. One form is shown in FIG. 3. Upon conversion to the two-chain form, as the activation peptide is not present in the precursor, the products are indistinguishable from Factor Xai or rXai.

PREPARATION OF THE INVENTIVE PEPTIDES

The genomic organization and coding sequence (except for nucleotides 1251-1300 which can be deduced from the Kaul et al. reference) for human Factor X are known and the cDNA has been retrieved and sequenced (Leytus, S. P., et al., *Proc Natl Acad Sci USA* (1984) 81:3699; Kaul, R. K., et al., *Gene* (1986) 41:311-314). The complete cDNA sequence is shown in FIG. 4.

Full-length Factor X cDNA are subcloned into M13mp18 or M13mp19 vectors for site-directed mutagenesis. (The correct sequence encoding Factor X is verified by dideoxy sequencing.) Standard modification techniques are now readily available i-n the art, and thus the sequence encoding Factor X is modified to obtain the DNA-encoding Factor X', Factor Xi, and Factor X'i.

The modified coding sequences for Factor X', Factor Xi and Factor X'i are then lighted into suitable expression vectors for recombinant production of the polypeptides. In the expression vectors, the prepro leader sequence is preferably retained for expression in compatible host cells such as mammalian hosts. If bacterial or yeast expression is desired, it may be desirable to substitute a compatible leader sequence, such as the penicillinase sequence in bacteria, or the alpha-factor sequence in yeast. Alternatively, an ATG start codon may be directly placed before amino acid 1 of the light chain-encoding sequence to produce an intracellular protein.

The choice of host and expression control system is governed by the nature of the desired result. If endogenous activation by proteolytic cleavage is desired, mammalian systems may be preferable. However, production in microorganisms which provide simplicity of culturing is not precluded. A wide variety of expression systems for recombinant DNA sequences is known in the art.

The modified DNA encoding Factor X', Factor Xi or Factor X'i is preferably provided with linkers for ligation into cloning and expression vectors. Techniques for preparation of such vectors are well understood in the art. The DNA encoding the desired Factor X', Factor Xi or Factor X'i is ligated in operable linkage with control sequences, including promoters, upstream enhancers, termination sequences, and so forth, depending on the nature of the intended recombinant host cells. Technology is currently available for expression of heterologous genes in a variety of hosts, including procaryotic hosts and various eucaryotes, including yeasts, mammalian or avian or insect cells, and plant cells. The choice of control sequences and markers in the expression vectors is selected appropriately to these hosts.

For example, in procaryotic hosts, various promoters, including inducible promoters such as the trp promoter and lambda phage $P_L$ promoter can be employed. Hybrid promoters such as the tac promoter, which contains the trp polymerase binding region in combination with the lac operator, can be used. Suitable markers are generally those related to antibiotic resistance. On the other hand, in mammalian cell cultures, commonly used promoters are virally derived, such as the early and late SV40 promoters and adenovirus promoters. Mammalian regulatable promoters, such as the metallothionein-II promoter may also be used. The metal othionein-II promoter is regulated by glucocorticoids or heavy metals. These promoter systems are compatible with typical mammalian hosts, the most commonly used of which is Chinese hamster ovary (CHO) cells.

Another commonly employed system is the baculovirus expression system compatible with insect cells. Plant cells, used in conjunction with, for example, the nopaline synthetase promoter, and yeast cells, used in conjunction with promoters associated with enzymes important in the glycolytic pathway, can also be employed. A number of suitable expression systems can be found in appropriate chapters in "Current Protocols in Molecular Biology," Ausubel, F. M., et al., eds., published by Wiley Interscience, latest edition.

Administration and Use

The Factor Xai peptides of the invention are prothrombinase inhibitors and are thus useful in procedures complicated by thrombosis and in conditions whose pathogenesis involves thrombin generation. These conditions include those involving arterial thrombosis, such as unstable (i.e., rest) angina and abrupt vessel closure during vascular interventions including coronary and peripheral angioplasty and atherectomy, and during and after vascular bypass procedures (peripheral and coronary), reocclusion after thrombolytic therapy for myocardial infarction, thrombotic stroke (stroke in evolution), and thrombosis due to vasculitis (Kawasaki's disease). Also included are conditions involving venous thrombosis, such as deep venous thrombosis of the lower extremities, pulmonary embolism, renal vein, hepatic vein, inferior vena cava thrombosis, and cavernous sinus thrombosis. Other target conditions are those involving diffuse activation of the coagulation system, such as sepsis with disseminated intravascular coagulation, disseminated intravascular coagulation in other settings, thrombotic thrombocytopenic purpura, and rare conditions of unknown etiology (*Lupus anticoagulant*).

The Factor Xai of the invention is also useful as an anticoagulant and anti-inflammatory for cardiopulmonary bypass, in harvesting organs, in preparation of blood products or samples and in transport and implantation of organs and associated treatment of the recipient. The Factor Xai, in a slow release form, is especially useful in indwelling intravascular devices (i.v.s, catheters, grafts, patches).

Thrombosis also plays a role in restenosis following vascular interventions such as angioplasty, atherectomy, or endarterectomy by directly or indirectly causing smooth muscle cell proliferation, and the Factor Xai of the invention is also useful in treating this condition.

Adult respiratory distress syndrome (ARDS) is thought to be an "endotoxin" disease in which a prothrombotic endothelium is likely to exist, with inflammatory and proliferative components; Factor Xai is also useful in treatment of ARDS.

The therapeutic Factor Xai peptides of the invention are formulated for administration using excipients conventional for administration of proteins, typically by injection, as set forth, for example, in *Remington's Pharmaceutical Sciences*, Mack Publishing Company, latest edition, Easton, Pa. For the antithrombosis effect, the Factor Xai proteins are administered systemically, preferably by injection, and preferably by intravenous injection. Dosage levels depend on a number of factors, including the condition of the subject and the specific Factor Xai embodiment chosen. However, suitable dosage ranges are on the order of 1-50 mg per patient per continuous injected dose. For injection, the protein is dissolved or suspended in liquid medium, for example, Hank's solution, Ringer's solution, dextrose solution, and various buffers. Additional excipients such as stabilizers can also be employed.

Besides injection, the peptides of the invention can be administered systemically, via suppository, oral administration, transmucosal administration, including intranasal sprays, and by slow release formulations. Additional formulation techniques include encapsulation formulations, such as liposomes.

In addition to utility as a therapeutic, the Factor Xai can be used to raise polyclonal antisera or to produce cells which can be fused to immortalizing partners to obtain sources of monoclonal antibodies specific for this peptide. These antibodies are useful as passive therapeutics or as diagnostic tools.

The following examples are intended to illustrate, but not limit the invention.

EXAMPLE 1

Construction of DNA Encoding Catalytically Inactive Forms of Recombinant Human Factor X (rXi)

A full length cDNA clone for human Factor X was obtained from Dr. W. R. Church, University of Vermont (FIG. 4). This cDNA encodes the amino acid sequence of FIG. 1 or an allelic variant. This human Factor X cDNA was cloned into EcoRI site of vector pBSII (Stratagene) to obtain pBSX. The HindIII-XbaI fragment of pBSX comprising the entire Factor X coding region was subcloned into the Hind III-XbaI site of vector M13mp19 (Mp19X). Oligonucleotide site-directed mutagenesis was then performed as described by Kunkel, T. A., et al., *Methods in Enzymol* (1987) 154:367.

The following forms were produced:

The oligomer TGC CGA GGG GAC GCC GGG GGC CCG CAC was used to convert serine ($S_{185}$) at position 185aa on the Factor X heavy chain to alanine ($A_{185}$) to obtain $rXiA_{185}$.

The oligomer ACC TAT GAC TTC AAC ATC GCC GTG CTC was used to convert aspartic acid ($D_{88}$) at position 88aa on the Factor X heavy chain to asparagine ($N_{88}$) to obtain the gene encoding $rXiN_{88}$.

Both oligomers were used to obtain the gene encoding $rXiN_{88}A_{185}$. (See FIG. 1 for location of these sites). Verification of oligonucleotide-directed mutagenesis was accomplished by dideoxy sequencing.

EXAMPLE 2

Construction of DNA Encoding the Truncated Precursor of Human Factor Xa (rX')

The cDNA of human Factor X (Mp19X) was converted to encode various truncated forms of human Factor Xa, collectively designated rX', by deletion of the activation peptide, by oligonucleotide site directed mutagenesis (Kunkel, T. A., et al., *Methods in Enzymol* (1987) 154:367). The following oligonucleotides employed with the corresponding amino acid changes are as follows:

rX'ΔO: ACC CTG GAA CGC AGG AAG AGG ATC GTG GGA GGC CAG GAA TGC, which aligned arginine ($R_{142}$) following the C-terminus of the Factor X light chain with isoleucine ($I_{53}$) 53aa of the Factor X activation peptide (1aa of the heavy chain);

rX'Δl: ACC CTG GAA CGC AGG AAG AGG AGA ATC GTG GAA TGC, which aligned this $R_{142}$ with arginine ($R_{52}$) of the Factor X activation peptide;

rX'Δ2: ACC CTG GAA CGC AGG AAG AGG CGG AAA AGA ATC GTG GGA GGC CAG GAA TGC, which extended R142 following the Factor X light chain by two amino acids arginine ($R_{143}$) and lysine ($K_{144}$) and aligned this terminus with $R_{52}$ of the Factor X activation peptide (FIG. 2);

rX'Δ3: ACC CTG GAA CGC AGG AAG AGG CCT AGG CCA TCT CGG AAA CGC AGG ATC GTG GGA GGC CAG GAA TGC, which extended $R_{142}$ following the Factor X light chain by seven amino acids, Proline ($P_{143}$) Arginine ($R_{144}$) Proline ($P_{145}$) Serine ($S_{146}$) Arginine ($R_{147}$) Lysine ($K_{148}$) Arginine ($R_{149}$) as described in Ehrlich, H. J., et al., *J Biol Chem* (1989) 264:14298, and aligned this terminus with $R_{52}$ of the Factor X activation peptides.

Verification of the oligonucleotide directed mutagenesis was accomplished by dideoxy sequencing.

As will be further described below, the precursor derived from rX'Δ2 was cleaved endogenously when recombinantly produced in CHO cells to obtain directly the activated form rXa. The precursor derived form rX'Δ0 was not cleaved endogenously in CHO cells when produced recombinantly. The precursor derived from rX'Δ1 or from rX'Δ3 was cleaved incompletely. The dimeric peptides derived from rX'Δ0, rX'Δ1 and rX'Δ3 were not active enzymatically.

EXAMPLE 3

Construction of DNA Encoding Catalytically Inactive Truncated Precursor (rX'i)

cDNA Factor X' constructs described in Example 2 were converted to encode the catalytically inactive forms of X' (rX'i) by oligonucleotide site-directed mutagenesis as described in Example 1. These constructs included $rX'i(\Delta2)N_{88}$ and $rX'i(\Delta2)N_{88}A_{185}$, as shown in FIG. 3.

EXAMPLE 4

Expression of the Genes Encoding Precursor (rX and rX')

The expression vector pRC/CMV (Invitrogen) was modified by replacing the CMV promoter with the SRα promoter (Takabe, Y., et al., Molec Cell Biol (1988) 8:466). The ClaI-XbaI fragment, filled in by Klenow polymerase at the ClaI site which contained the SRα promoter was isolated from the expression vector pBJ1 (Lin, A., et al., *Science* (1990) 249:677 and available from M. Davis, Stanford University) and subcloned into the NruI-XbaI site of pRC/CMV creating expression vector pBN. The StuI fragment of pBN, comprising the SRα promoter, bovine growth hormone polyadenylation site and M13 origin or replication was subcloned into the StuI site of pSV2DHFR generating expression vector pBD. The Mp19 SmaI-EcoRV fragments of the precursor DNAs described in examples were subcloned into the Klenow polymerase-filled-in XbaI site of pBN and pBD.

The resulting expression vectors were transfected into CHO by lipofection (BRL). Selection for transfected clones was by either 1 mg/ml G418 Neomycin (Gibco) or 25 ng/ml Methotrexate (Sigma). Single clones were isolated by cloning cylinders, expanded and expression levels were determined on 24 hour serum free medium by a standard solid phase antibody capture assay (ELISA) as described by Harlow, E., and Lane, D., in *Antibodies* (1988), Cold Spring Harbor Laboratory, N.Y. The ELISA utilized a primary antibody of rabbit polyclonal antihuman Factor X (STAGO, American Diagnostics Inc.) and a rabbit-specific secondary antibody of peroxidase conjugated goat IgG.

Clones from constructs pBNX, pBNX'ΔO, pBNX'Δ1, pBNX'Δ2, and pBNX'Δ3 were expanded to confluency in T-75 tissue culture flasks in RPMI medium supplemented with 10% fetal bovine serum, Penicillin, Streptomycin, Glutamine and 10 μg/ml vitamin K, washed four times with serum free medium and incubated overnight with serum free medium.

Post incubation the medium was harvested, centrifuged at 3000 rpm and 2 ml was precipitated with 10% Trichloracetic acid (TCA). The TCA pellet was washed three times with 100% Acetone, resuspended to 0.05 ml SDS-PAGE sample buffer or 0.05 m SDS- PAGE sample buffer with 1M β Mercaptoethanol. Duplicate 10 μl aliquots were electrophoresed on 12% SDS polyacrylamide gels and transferred to Immobilon filters (Millipore). Western blot analysis was performed with the primary human Factor X polyclonal rabbit sera (STAGO, American Diagnostics, Inc.) at a 1/4000 dilution in 1% nonfat dry milk, 0.1% NP40, 10 MM Tris-HCl pH 7.5, 150 mm NaCl. The secondary antibody was $^{125}$I labeled Fab donkey antirabbit IgG (Amersham). Autoradiography was overhight at −70° C. with an intensifier screen.

Figure 5A:
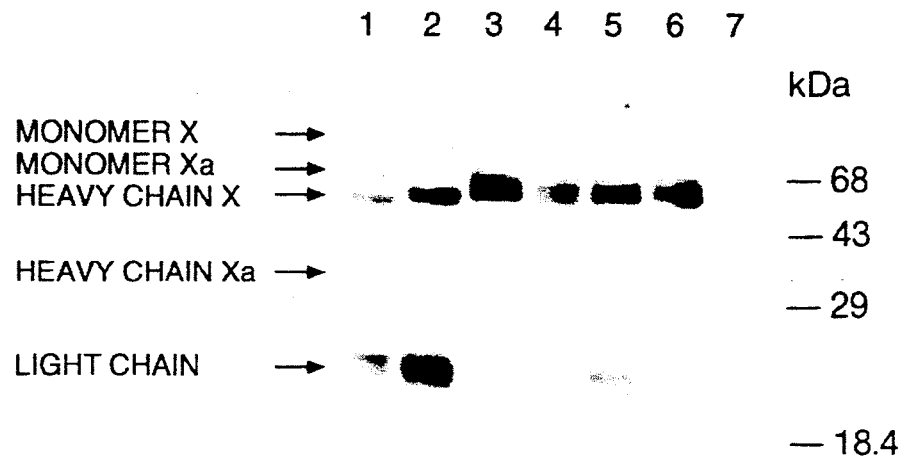
FIGS. 5(a) and 5(b) are a Western blot of recombinantly produced, potentially active Factor X and Factor Xa.
Figure 5B:
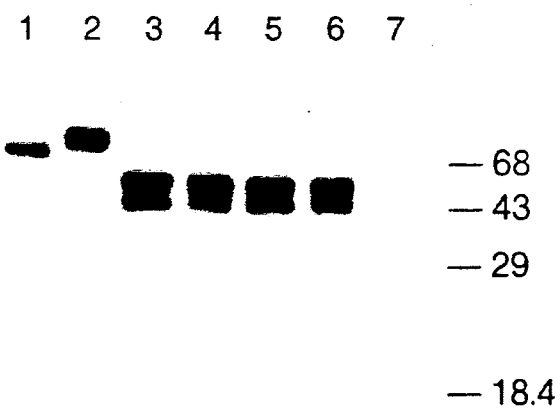

FIG. 5 shows Western blot analysis of products derived from rX, rX'Δ0, rX'Δ1, rX'Δ2, rX'Δ3 and CHO control medium. FIG. 5a shows reduced and FIG. 5b nonreduced forms of these recombinant proteins. Lane 1, 0.7 μg native human Factor X (Dr. C. Esmon, OMRF, University of Oklahoma); Lane 2, rX; Lane 3, rX'Δ0; Lane 4, rX'Δ1; Lane 5, rX'Δ2; Lane 6, rX'Δ3; Lane 7, CHO control medium.

FIG. 5a shows that the recombinant products of rX and rX'Δ2, are dimeric proteins which are separable under reducing conditions. The products of expression of rX'Δ0, rX'Δ1 and rX'Δ3 apparently are largely single-chain products. In FIG. 5b, it is apparent that the expression products of the X'-encoding gene are of lower molecular weight than rX or native Factor X.

EXAMPLE 5

Expression of the Genes Encoding Inactivated Recombinant Human Factor X (rXi and rX'i)

The X' form chosen for conversion to the inactive form was the rX'Δ2 form shown in FIG. 4. pBN-derived cell lines for rX, rX'(Δ2), rXiN$_{88}$A$_{185}$, rXiA$_{185}$, rX'i(Δ2)N$_{88}$A$_{185}$ and were grown to confluency in 800 cm$^2$ roller bottles as described in Example 4, washed four times with serum free medium and incubated overnight with 50 ml serum-free medium. The medium was replenished and harvested daily.

Consecutive harvests were pooled, centrifuged at 3000 rpm and passed directly through a Factor X-specific monoclonal antibody (Mab) affinity column (Mab717) supplied by Dr. C. Esmon (OMRF, University of Oklahoma). The bound "Factor X" was eluted from the Mab717 column with 80% ethylene glycol, dialyzed against 10 mM Tris HCl, pH 7.5, 150 mM NaCl and concentrated on a centricon 10 filtration unit (Amicon). "Factor X" protein concentrations were determined by ELISA as described in Example 4 utilizing serial dilution with comparison to a standard preparation of human Factor X (Haematologic Technologies, Inc., C. Esmon, OMRF, University of Oklahoma).

Figure 6:
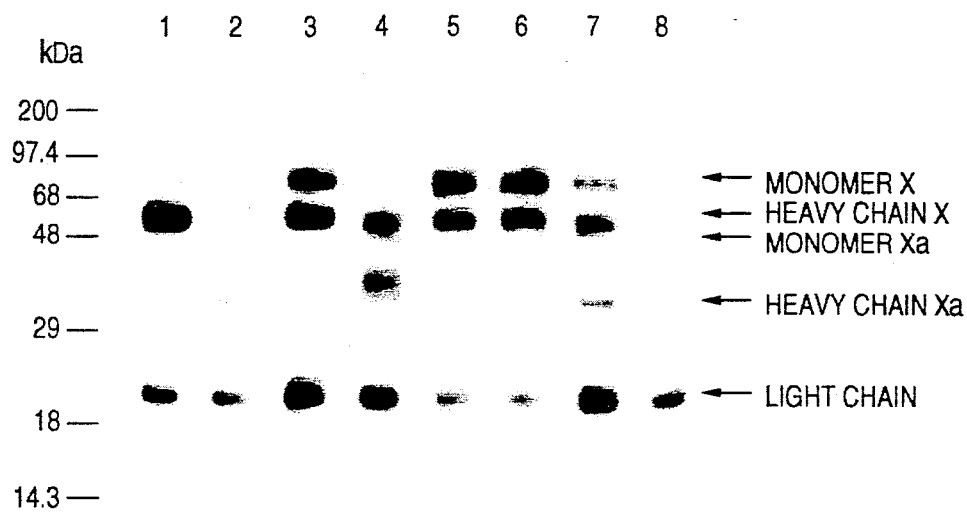
FIG. 6 is a Western blot of recombinantly produced, inactivated forms of Factor X and Factor Xa.
Figure 7A:
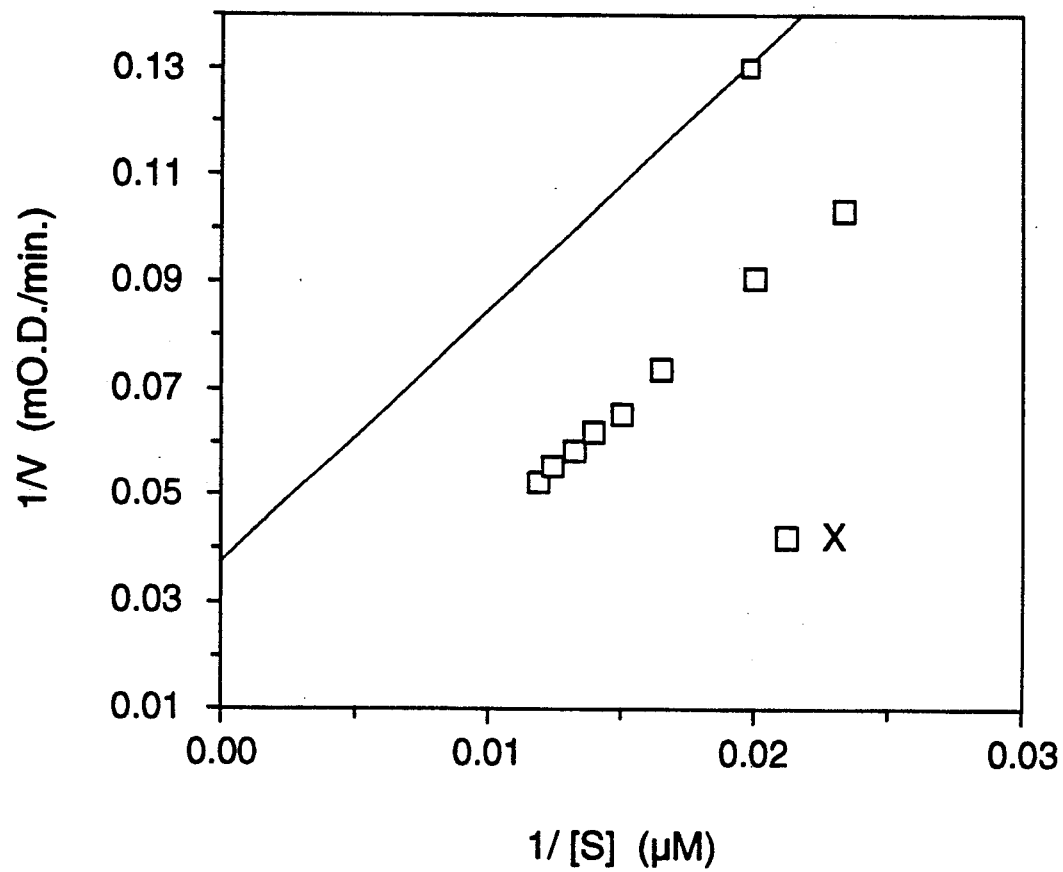
FIGS. 7 (a), 7(b), 7(c) and 7(d) are a series of Lineweaver-Burk plots showing the enzymatic activity of native and recombinantly produced Factor X converted to activated form.
Figure 7B:
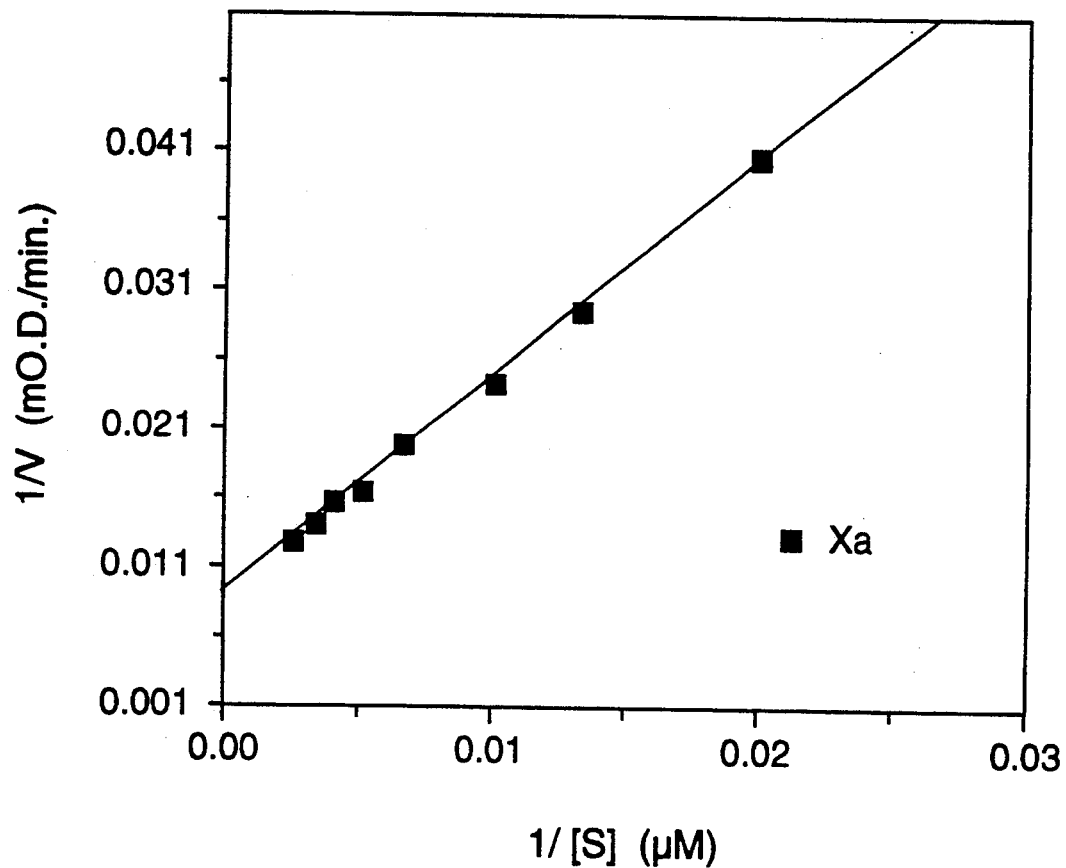
Figure 7C:
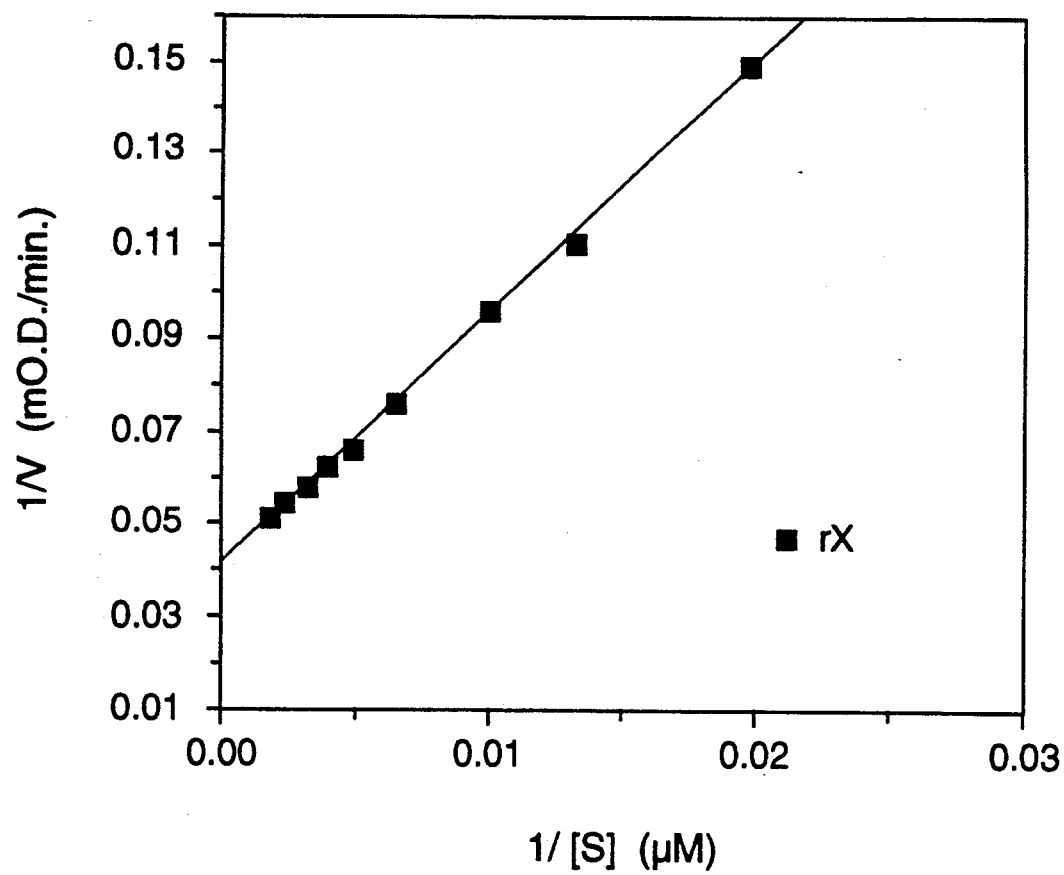
Figure 7D:
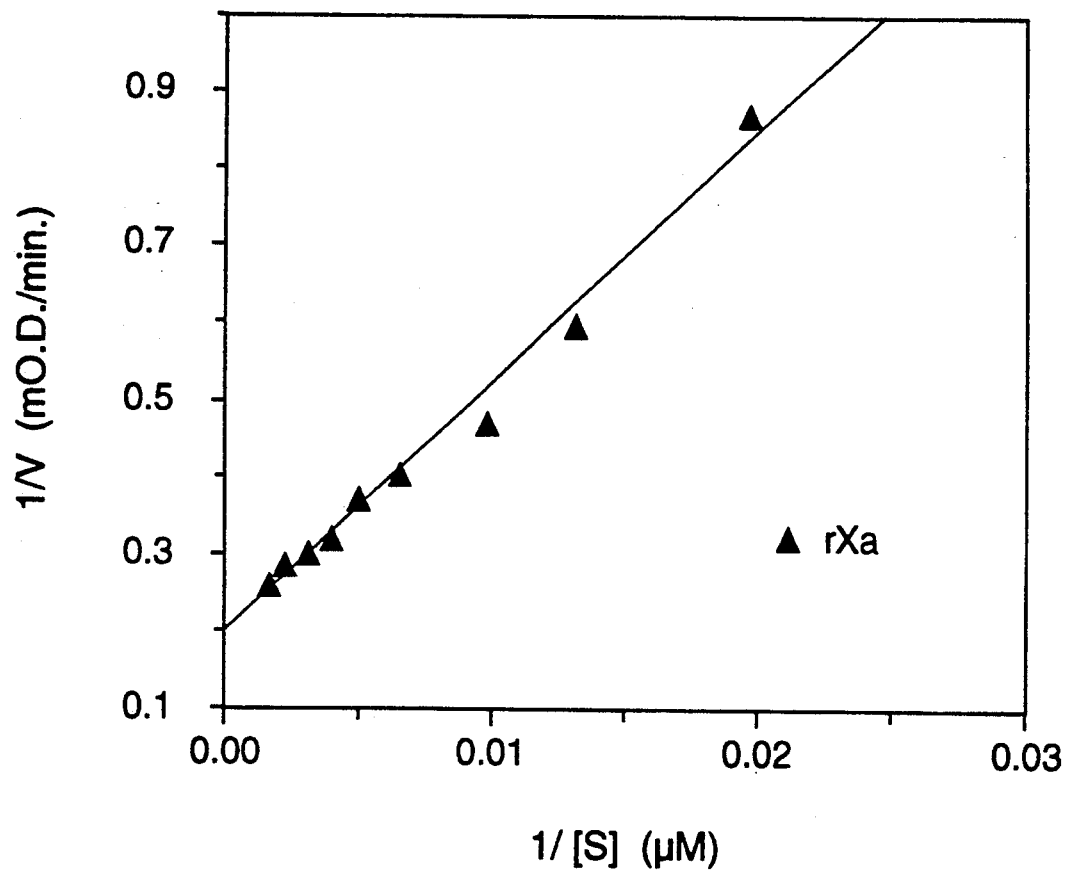

The purified proteins were characterized by Western blot analysis as outlined in Example 4. FIG. 6 shows a Western blot of these β-mercaptoethanol-reduced, Mab 717 purified recombinant human Factor X analogs. Lane 1, 0.1 μg human X (Haematologic Technologies, Inc.); Lane 2, 0.1 μg human Xa (Haematologic Technologies, (Inc.); Lane 3, 0.1 μg rX; Lane 4, 0.16 μg rX'Δ2; Lane 5, 0.13 μg rXiN$_{88}$A$_{185}$; Lane 6, 0.15 μg rXiA$_{185}$; Lane 7, 0.187 μg rX'i(Δ2)N$_{88}$, Lane 8, 0.05 μg rX'i(Δ2)N$_{88}$A$_{185}$.

It is evident that, under reducing conditions, human X and human Xa are in dimeric form; human Xa shows a lower molecular weight form of the heavy chain due to the absence of the activation peptide. Recombinant human X in lane 3 is similar to native human X, however some single chain precursor is still evident. In lane 4, recombinant rX'Δ2 also shows cleavage to the heavy and light chains. In lanes 5 and 6, the modified recombinant Xi proteins behave in a manner similar to recombinant human X. As expected, lanes 7 and 8 show the presence of monomer, heavy and light chains derived from the proteolytic cleavage of X'i.

EXAMPLE 6

Enzymatic Analysis of Recombinant Human Factor X

The kinetic measurement of chromozym X (N-methoxycarbonyl-D-norleucyl-glycyl-arginine-4-nitranilide acetate, Boehringer Mannheim) hydrolysis by native human Factor X, Xa, recombinant X (rX), rX'Δ0, rX'Δ1, rX'Δ2, rX'Δ3, rXiN$_{88}$A$_{185}$, rXiN$_{88}$, rX'i(Δ2)N$_{88}$A$_{185}$ and inactivated bovine Xa, Xai-APMSF supplied by Dr. C. Esmon (OMRF, University of Oklahoma) (Skogen, W. F., et al., *J Biol Chem* (1984) 259:2306) were examined at room temperature in 96-well microtiter plates on a Molecular Devices Vmax spectrophotometer. The absorbance at 405 nM was monitored continuously and the reaction velocities were determined directly by the machine and plotted with the Enzfitter program (Elsevier Press). Protein concentrations were determined by ELISA (Example 5). All enzymes were diluted to the appropriate concentrations in 0.1% bovine serum albumin (BSA) 50 mM Tris HCl, pH 8.0, 150 mM NaCl. Duplicate reactions were carried out in 50 mM Tris HCl, pH 8.0, 150 mM NaCl and 2.5 mM CaCl$_2$. All recombinant human Factor X's were Mab717-purified (Example 5) except for RX'Δ0, rX'Δ1, and rX'Δ3 which were purified using QAE-Sepharose (Pharmacia) concentrated (Skogen, W. F., et al., *J Biol Chem* (1984) 259:2306).

The recombinantly produced peptides derived rXiA$_{185}$ were treated by preincubation for 5 minutes with Russell's viper venom to convert them to the Xa or Xai form. Peptides derived from the rX'Δ0, rX'ΔI, rX'Δ2 and rX'Δ3 vectors were not treated in this fashion.

FIG. 7 is a comparison of Lineweaver-Burk plots for native human Factor X and Xa and activated forms derived from recombinant human rX and rX'. FIG. 7a, human X; FIG. 7b, human Xa; FIG. 7c, human rX (treated with Russell's viper venom protease); FIG. 7d, human rX' (not treated with protease). FIG. 8 also compares the Kcat and Km values of the recombinantly produced human Factor X's to the native human Factor X and Xa supplied by Haematologic Technologies, Inc. Of course, none of the inactivated forms give values; of the rX' forms, only rX'Δ2 showed activity.

EXAMPLE 7

Factor X Dependent Prothrombinase Complex Activity of Human X, Xa and Recombinant Human rX and rX'

Factor X dependent prothrombinase complex activity was determined by measuring the rate of chromozyme TH (tosyl-glycyl-prolyl-arginine-4-nitroanilide acetate, Boehringer Mannheim) hydrolysis by thrombin at room temperature in a 96-well microtiter plate on a Molecular Devices Vmax spectrophotometer. The absorbance at 405 nM was continuously monitored and the initial one minute reaction velocities were determined directly by the machine and plotted using the Enzfitter program (Elsevier). Reaction mixtures were performed in triplicate with $0.05 \times 10^{-4}$M to $1.5 \times 10^{-9}$M "Factor X," determined by ELISA (Example 5), $0.5 \times 10^{-6}$M human prothrombin (STAGO, American Diagnostics, Inc.) $7.5 \times 10^{-9}$M human factor Va (Haematologic Technologies, Inc.), $20 \times 10^{-6}$M phosphocholine/phosphoserine 75%/25% (PCPS) (supplied by Dr. W. R. Church, University of Vermont), or equivalent amounts of rabbit brain cephalin (Sigma) (Example 8), 0.1% BSA (Sigma), $0.1 \times 10^{-3}$M chromozym TH (Boehringer Mannheim), 25 mM Tris HCl, pH 7.5, 150 mM NaCl and 5 mM CaCl$_2$.

Figure 9A:
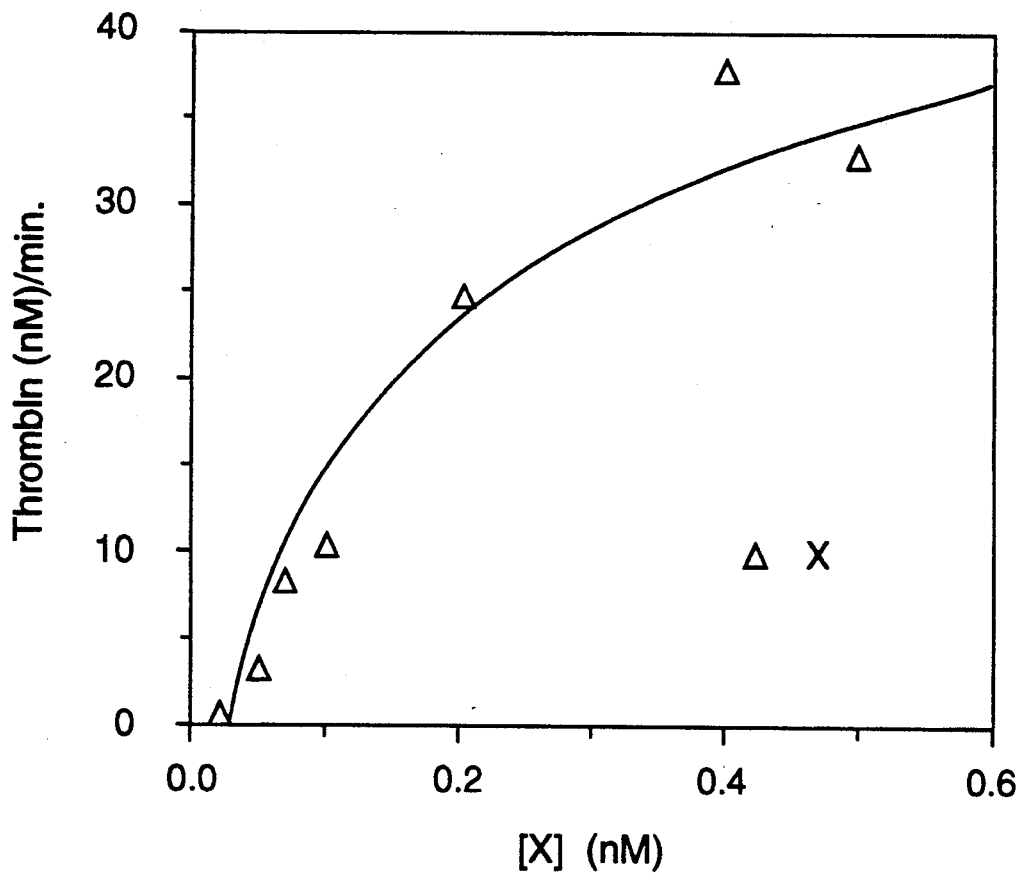
FIGS. 9(a) 9(b),9)c) and 9(d) are a comparison of prothrombinase complex activity of various Factor X forms.
Figure 9B:
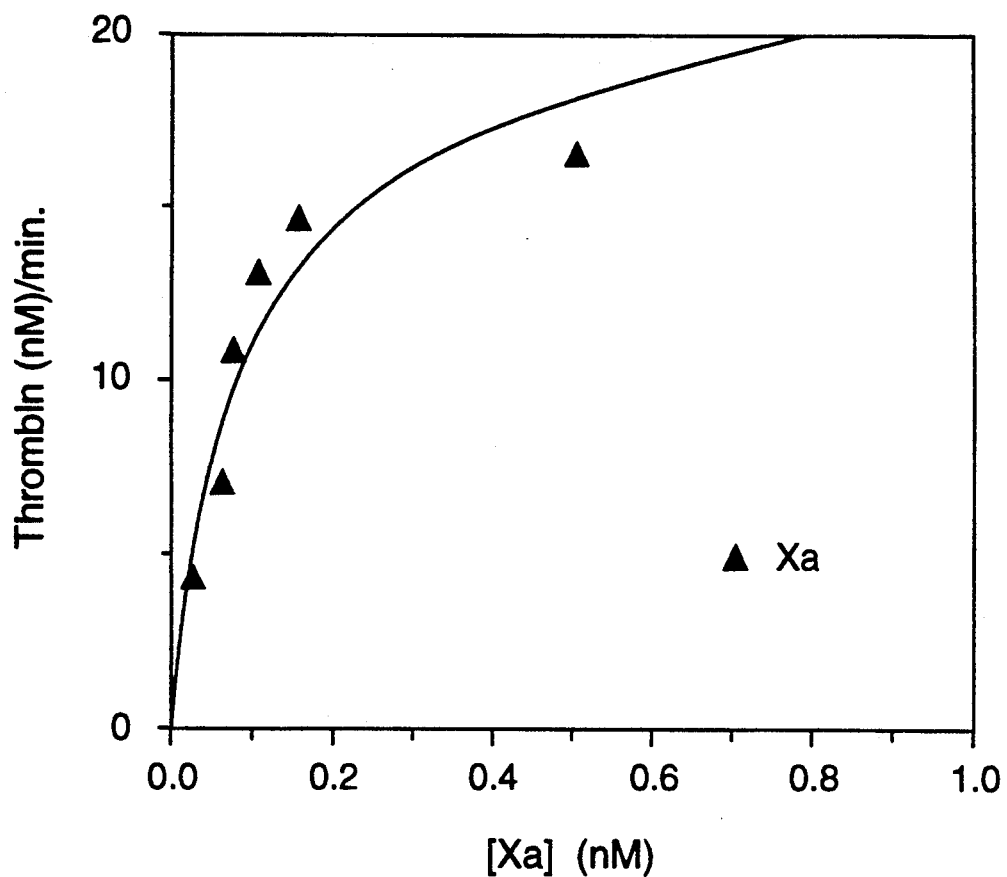
Figure 9C:
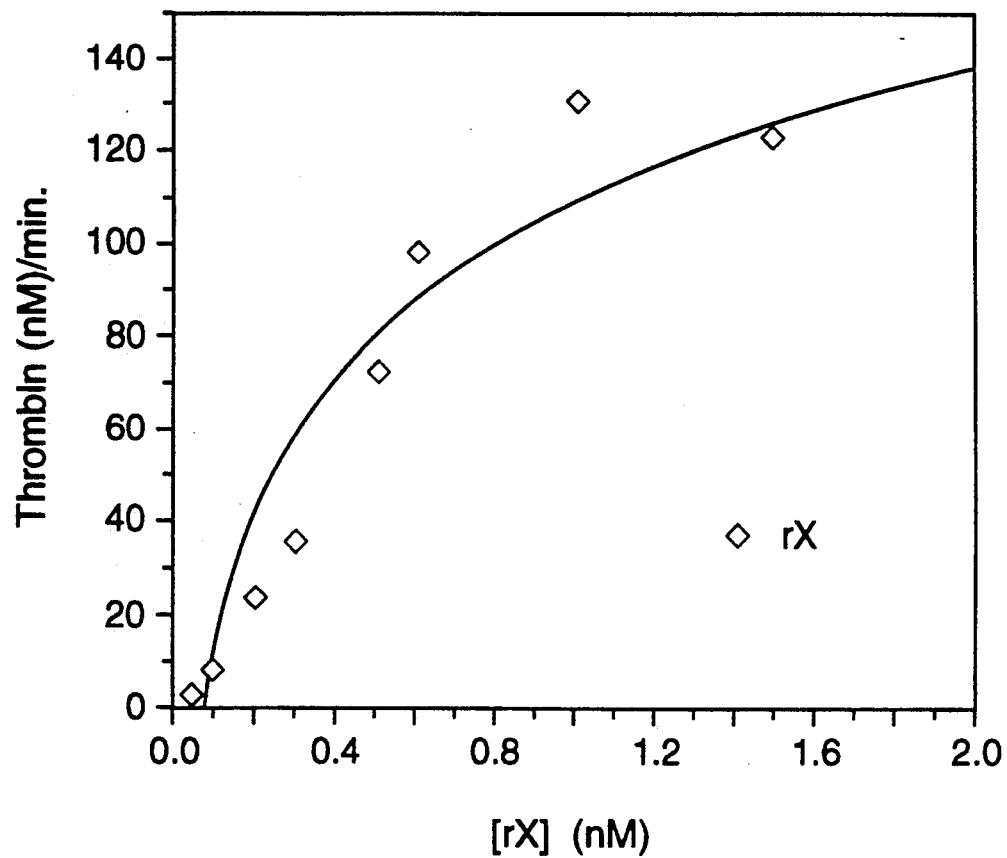
Figure 9D:
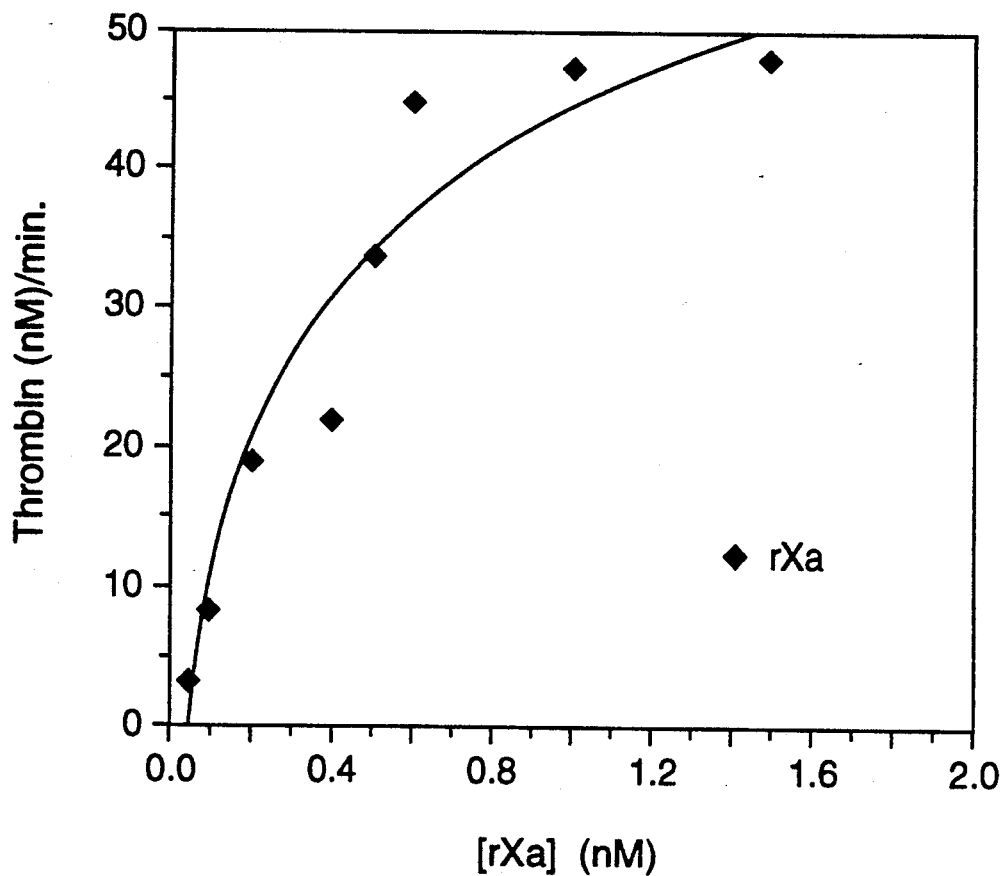

Human Factor rX and rX' dependent prothrombinase complex activity utilized PCPS and human Factor X and Xa dependent prothrombinase complex activity utilized cephalin. Human Factor X and rX were preincubated for 5 minutes with Russell's viper venom (Haematologic Technologies, Inc.). Thrombin hydrolysis of chromozym TH as determined by increase of fluorescence signal, was linear throughout the experimental protocol. No observable rates were shown for rXiN$_{88}$A$_{185}$ at $59.2 \times 10^{-4}$M, rX'iN$_{88}$A$_{185}$ at $10.2 \times 10^{-9}$M, or for bXai-APMSF at $1 \times 10^{-9}$M FIG. 9 compares Factor X dependent prothrombinase complex activity of human X (FIG. 9a), human Xa (FIG. 9b) (Haematologic Technologies, Inc.), recombinant human rX (after treatment with protease) (FIG. 9c) and recombinant human rX'Δ2 (after no protease treatment) (FIG. 9d). All are comparably active.

EXAMPLE 8

Coagulation of Plasma

Figure 10:
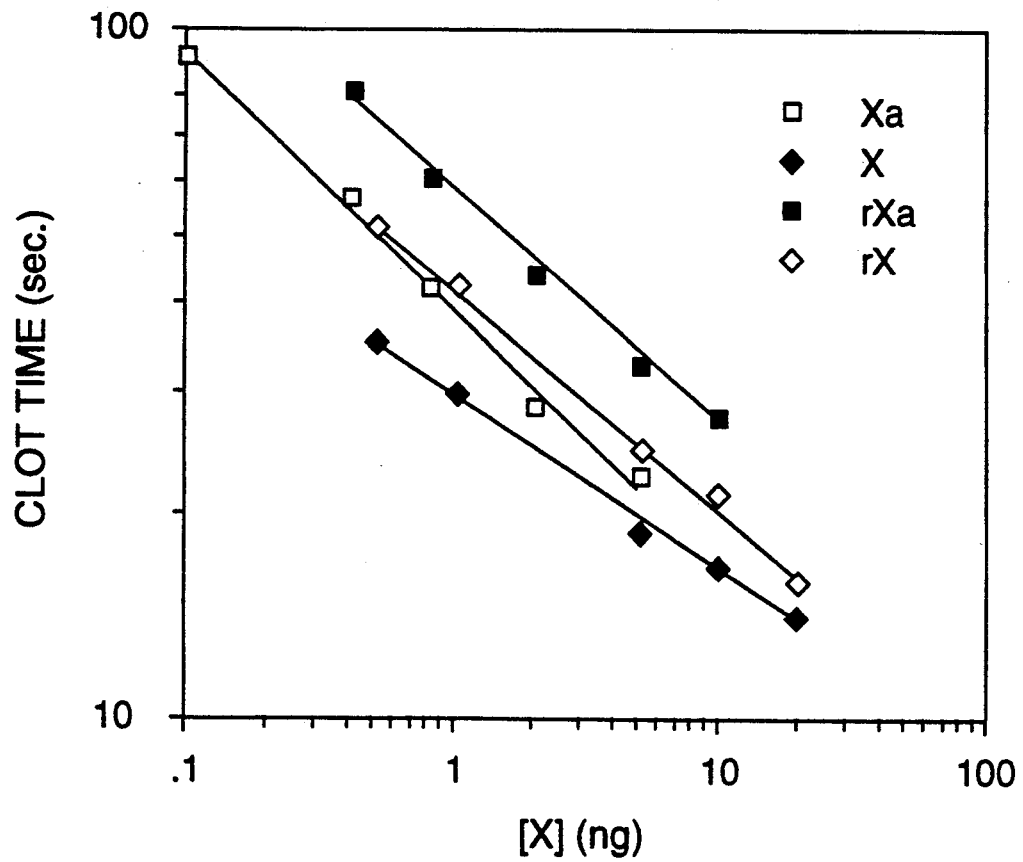
FIG. 10 shows the result of a two-stage prothrombin clotting assay for various forms of Factor X.

Mab717 purified rX and rXa were assayed for plasma coagulation activity in an automated two-stage prothrombin assay on a MLA Electra 800 fibrometer. Enzyme protein concentrations were determined by ELISA (Example 5) and diluted in 0.1% BSA, 150 mM NaCl prior to use. Bovine Factor X and Factor VII deficient plasma (Sigma) and rabbit brain cephalin (Sigma) were prepared according to manufacturers' instructions. Russell's viper venom 0.1 g/ml was added to human X and rX assays. The reaction mixture comprised 0.1 ml Factor X, 0.1 ml 50 mM NaCl, 0.1 ml cephalin and 0.1 ml 25 mM CaCl$_2$. Duplicates were performed on each concentration and the average of two experiments were calculated. FIG. 10 compares the plasma coagulation activity of human X, human Xa, human rX and human rXa. Human rX was calculated to be 45% as active as human X and human rXa was calculated to be 32% as active as human Xa.

EXAMPLE 9

Inhibition of Prothrombinase Complex Activity by rXiN$_{88}$A$_{185}$ Human rX'i(Δ2) N$_{88}$A$_{185}$ and Bovine bXai-APMSF Inhibition of native human Factor X dependent prothrombinase complex activity by human rXiN$_{88}$A$_{185}$ and inhibition of native human Factor $5 \times 10^{-9}$M Xa dependent prothrombinase complex activity by human rX'i(Δ2)N$_{88}$A$_{185}$ and bovine bXai-APMSF (C. Esmon, OMRF, University of Oklahoma) was tested as detailed in Example 7. It is necessary to compare directly X with Xi and Xa with Xai because of kinetic factors and the strength of the complex once formed. Human rXiN$_{88}$A$_{815}$ was preincubated for 5 minutes with 0.1 μg/ml Russell's viper venom. The human Factor X and Xa concentrations were $1 \times 10^{-9}$M.

Figure 11:
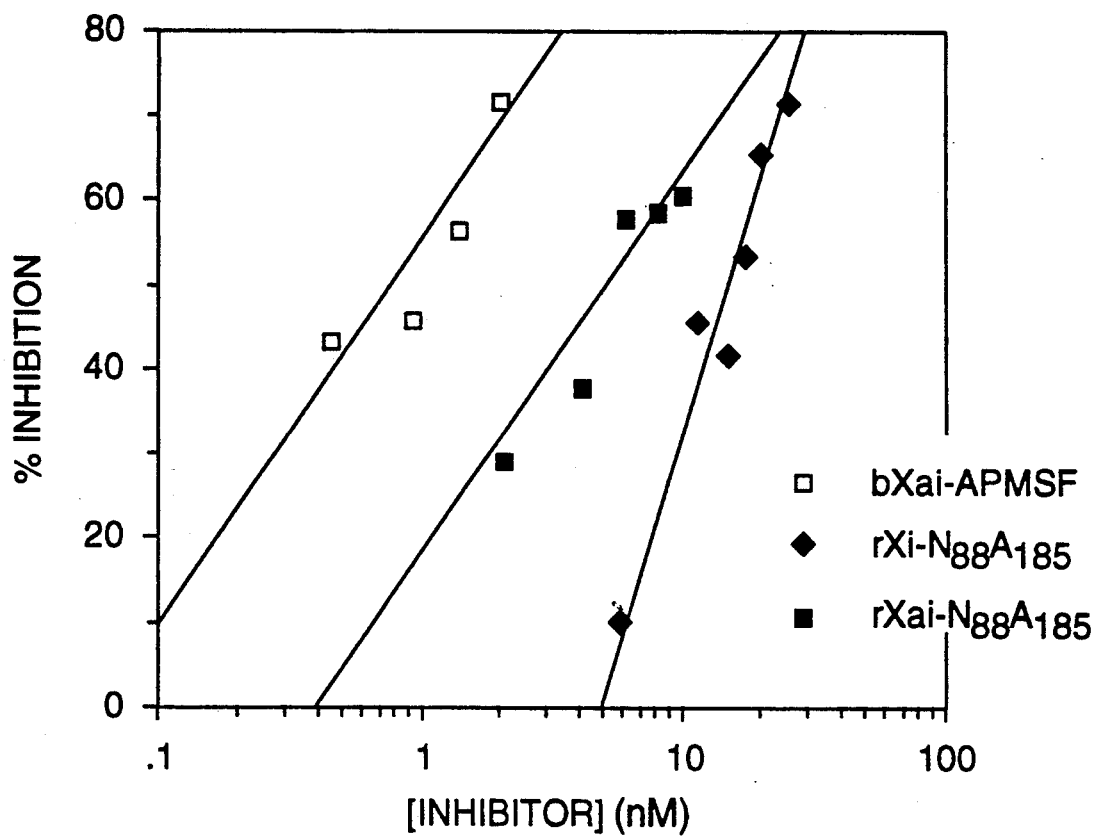
FIG. 11 shows inhibition of prothrombinase complex formation by inactive forms of Factor X.

FIG. 11 shows the concentration dependent inhibition of the human Factor Xa dependent prothrombinase complex by bXai-APMSF, rX'i(Δ2)N$_{88}$A$_{185}$ and inhibition of the human Factor X dependent prothrombinase complex by rXiN$_{88}$A$_{185}$. 50% inhibition by bXai-APMSF was obtained at $0.9 \times 10^{-9}$M, 50% inhibition by rX'i(Δ2)N$_{88}$A$_{185}$ was obtained at $6 \times 10^{-9}$M and 50% inhibition by rXiN$_{88}$A$_{185}$ was obtained at $10.6 \times 10^{-9}$M.

I claim:

1. A two chain Factor Xai peptide modified from the native amino acid sequence of light chain positions 1-139 and heavy chain positions 1-254 of FIG. 1, wherein said Factor Xai is capable of competing with Factor Xa in the formation of prothrombinase complex and wherein said Factor Xai does not result in proteolytic activity when included in said complex, wherein the serin residue corresponding to that at position 185 of the heavy chain in FIG. 1 is replaced by a different amino acid and/or the aspartic acid residue at the position corresponding to that of position 88 of the heavy chain shown in FIG. 1 is replaced by an alternate amino acid.

2. The factor Xai of claim 1 wherein the replacement for serine is an alanyl residue and the replacement for aspartic acid is an asparagine residue.

3. A single-chain polypeptide which is convertible to Factor Xai by proteolysis; said Factor Xai being a modified form of the amino acid sequence of light chain positions 1-139 and heavy chain positions 1-254 of FIG. 1 wherein said Factor Xai is capable of competing with Factor Xa in the formation of a prothombinase complex and wherein said Factor Xai does not result in proteolytic activity when included in said complex, wherein the serine residue corresponding to that at position 185 of the heavy chain in FIG. 1 is replaced by an alternate amino acid and/or the aspartic acid residue at the position corresponding to that of position 88 of the heavy chain shown in FIG. 1 is replaced by an alternate amino acid.

4. The polypeptide of claim 3 wherein said light chain and heavy chain are linked by an amino acid sequence consisting essentially of a proteolytic cleavage site at the C-terminus of said light chain ligated directly to the N-terminus of said heavy chain.

5. The polypeptide of claim 4 wherein said cleavage site is RKRRKR.

6. A pharmaceutical composition for the prevention or treatment of thrombosis in animal subject, which composition comprises an amount of the Factor Xai of claim 1 effective to ameliorate or prevent thrombosis in admixture with a pharmaceutically acceptable excipient.

7. A method to prevent or treat thrombosis in an animal subject which method comprises administering to a subject in need of such treatment an effective amount of the Factor Xai of claim 1 or a pharamaceutical composition thereof.

8. A method to prepare Factor Xai useful in treatment of thrombosis, which method comprises
  contacting the precursor polypeptide of claim 3 with an amount of a protease effective to cleave said precursor; and
  recovering the Factor Xai produced.

9. The method of claim 8 wherein said protease is contained in a Russell viper venom extract.

10. A Factor Xai prepared by the method of claim 8.

* * * * *